US00PP16694P2

(12) United States Plant Patent
Michalik

(10) Patent No.: US PP16,694 P2
(45) Date of Patent: Jun. 20, 2006

(54) ***GERANIUM* PLANT NAMED 'SHALET'**

(50) Latin Name: *Pelargonium×hortorum*
Varietal Denomination: Shalet

(75) Inventor: Andrea Michalik, Dresden (DE)

(73) Assignee: Elsner pac Jungpflanzen, Dresden (DE)

( * ) Notice: Subject to any disclaimer, the term of this patent is extended or adjusted under 35 U.S.C. 154(b) by 47 days.

(21) Appl. No.: 11/073,462

(22) Filed: Mar. 5, 2005

(51) Int. Cl.
*A01H 5/00* (2006.01)

(52) U.S. Cl. ..... Plt./329

(58) Field of Classification Search ..... Plt./329
See application file for complete search history.

*Primary Examiner*—Kent Bell
(74) *Attorney, Agent, or Firm*—C. A. Whealy

(57) ABSTRACT

A new and distinct cultivar of Zonal *Geranium* plant named 'Shalet', characterized by its upright, outwardly spreading and rounded plant habit; vigorous growth habit; freely branching and flowering habit; red purple-colored sterile flowers that are not persistent; and good garden performance and plants flower well under partial shade conditions.

1 Drawing Sheet

Botanical designation: *Pelargonium×hortorum.*
Cultivar denomination: 'Shalet'.

CROSS-REFERENCE TO RELATED APPLICATIONS

The present application is co-pending with the following related application: *Geranium* Plant Named 'Share'; Andrea Michalik, applicant.

BACKGROUND OF THE INVENTION

The present invention relates to a new and distinct cultivar of Zonal *Geranium* plant, botanically known as *Pelargonium×hortorum,* and hereinafter referred to by the name 'Shalet'.

The new Zonal *Geranium* is a product of a planned breeding program conducted by the Inventor in Dresden, Germany. The objective of the breeding program was to develop new Zonal *Geraniums* that flower well under partial shade conditions.

The new Zonal *Geranium* originated from a cross-pollination made by the Inventor in 2001of two proprietary selections of *Pelargonium×hortorum,* not patented. The cultivar Shalet was discovered and selected by the Inventor as a flowering plant within the progeny from the stated cross-pollination in a controlled environment in Dresden, Germany in 2002.

Asexual reproduction of the new cultivar by terminal cuttings in a controlled environment in Dresden, Germany since January, 2002 has shown that the unique features of this new Zonal *Geranium* are stable and reproduced true to type in successive generations of asexual reproduction.

SUMMARY OF THE INVENTION

The following traits have been repeatedly observed and are determined to be the unique characteristics of 'Shalet'. These characteristics in combination distinguish 'Shalet' as a new cultivar and distinguish it from other known Zonal *Geranium* cultivars:

1. Upright, outwardly spreading and rounded plant habit.
2. Vigorous growth habit.
3. Freely branching and flowering habit.
4. Red purple-colored sterile flowers that are not persistent.
5. Good garden performance and plants flower well under partial shade conditions.

Plants of the new Zonal *Geranium* differ primarily from plants of the parent selections in flower coloration.

Plants of the new Zonal *Geranium* can be compared to plants of the cultivar Share, disclosed in U.S. Plant patent application Ser. No. 11/073,463. In side-by-side comparisons conducted in Dresden, Germany, plants of the new Zonal *Geranium* differed from plants of the cultivar Share in the following characteristics:

1. Plants of the new Zonal *Geranium* had glossier foliage than plants of the cultivar Share.
2. Plants of the new Zonal *Geranium* had longer peduncles than plants of the cultivar Share.
3. Plants of the new Zonal *Geranium* had fewer flowers per umbel than plants of the cultivar Share.
4. Plants of the new Zonal *Geranium* and the cultivar Share differed in flower coloration as plants of the cultivar Share had red-colored flowers.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal *Geranium*. The photograph comprises a side perspective view of typical flowering plants of 'Shalet' grown in a container.

DETAILED BOTANICAL DESCRIPTION

Plants of the cultivar Shalet have not been observed under all possible environmental conditions. The phenotype may vary somewhat with variations in environment, such as temperature and light intensity, without, however, any variance in genotype.

The aforementioned photograph, following observations and averaged measurements describe plants grown during the spring in containers in Dresden, Germany, and under commercial practice in a glass-covered greenhouse with day temperatures about 18° C., night temperatures about 16° C. and light levels about 60,000 lux. Plants used for the photograph were about seven months old and plants used for the detailed botanical description were about four to five months old. In the following description, color references are made to The Royal Horticultural Society Colour Chart, 1995 Edition, except where general terms of ordinary dictionary significance are used.

Botanical classification: *Pelargonium×hortorum* cultivar Shalet.

Parentage:

*Female, or seed, parent.*—Proprietary selection of *Pelargonium×hortorum,* not patented.

*Male, or pollen, parent.*—Proprietary selection of *Pelargonium×hortorum,* not patented.

Propagation:

*Type cutting.*—Terminal cuttings.

*Time to initiate roots.*—Summer: About 10 days at 23° C. Winter: About 12 days at 23° C.

*Time to produce a rooted young plant.*—Summer: About 28 days at 23° C. Winter: About 30 days at 23° C.

*Root description.*—Fine, fibrous; white in color.

*Rooting habit.*—Freely branching, moderately dense.

Plant description:

*General appearance.*—Upright, outwardly spreading and rounded plant habit; uniform; densely foliated.

*Growth and branching habit.*—Vigorous growth habit. Freely basal branching, pinching is not required.

*Plant height, to top of umbels.*—About 25 to 28 cm.

*Plant height, to top of foliar plane.*—About 18 to 21 cm.

*Plant width.*—About 30 to 35 cm.

*Foliage description.*—Arrangement: Alternate or opposite; simple. Length: About 5 cm. Width: About 8 cm. Shape: Reniform. Apex: Rounded. Base: Cordate; open. Margin: Palmately lobed. Venation pattern: Palmate. Texture, upper surface: Pubescent. Texture, lower surface: Smooth, glabrous. Color: Developing foliage, upper surface: 137B. Developing foliage, lower surface: 138B. Fully expanded foliage, upper surface: 137A; venation, similar to lamina. Fully expanded foliage, lower surface: 137C; venation, 138B. Zonation pattern: None observed. Petiole: Length: About 9 to 12 cm. Diameter: About 3 mm. Texture, upper and lower surfaces: Pubescent. Color, upper and lower surfaces: Close to 144A.

Flower description:

*Flower arrangement.*—Red purple-colored flowers; single flat and roughly rotate flowers arranged in rounded hemispherical umbels arising from apical leaf axils. Umbels displayed above the foliage on strong peduncles. Flowers face upright to outwardly. Flowers not persistent. Flowers not fragrant.

*Quantity of flowers.*—Freely flowering habit; about 12 to 23 flower buds and open flowers per umbel.

*Flowering season.*—Year-round under greenhouse conditions. In the garden in Dresden, Germany, flowering is continuous from April until frost in the fall.

*Flower longevity.*—Individual flowers last about five to seven days on the plant.

*Umbel height.*—About 6 cm.

*Umbel diameter.*—About 11 cm.

*Flower diameter.*—About 4 cm.

*Flower depth* (*height*).—About 1 cm.

*Flower buds.*—Length: About 1.3 cm. Diameter: About 4 mm. Shape: Elliptic. Color: Close to 144A.

*Petals.*—Quantity per flower: Five. Length: About 2 cm. Width: About 1.2 to 1.8 cm. Shape: Obovate. Apex: Rounded. Base: Attenuate. Margin: Entire. Texture, upper and lower surfaces: Smooth, glabrous. Color: When opening, upper surface: 57A. When opening, lower surface: 57B. Fully opened, upper surface: 57B; towards the base, close to 155D; venation, 60B. Fully opened, lower surface: 57B; towards the base, close to 155D; venation, close to 57B.

*Sepals.*—Quantity per flower: Five, arranged in a single whorl. Length: About 1 cm. Width: About 3 to 4 mm. Shape: Lanceolate. Apex: Rounded. Base: Obtuse. Margin: Entire. Texture, upper surface: Smooth, glabrous. Texture, lower surface: Pubescent. Color, upper and lower surfaces: Close to 144A.

*Peduncle* (*umbel stem*).—Length: About 17 to 30 cm. Diameter: About 4 mm. Strength: Strong. Texture: Pubescent. Color: Close to 144A.

*Pedicel* (*individual flower stem*).—Length: About 3 cm. Diameter: About 1.5 to 2 mm. Strength: Strong. Texture: Pubescent. Color: Close to 144A.

*Reproductive organs.*—Androecium: Stamen quantity per flower: Five. Anther length: About 2 mm. Anther shape: Oval. Anther color: Close to 155D. Pollen amount: Scarce. Pollen color: Orangish. Gynoecium: Pistil quantity per flower: One. Pistil length: About 1 to 2 mm. Stigma color: Reddish. Style color: Reddish. Ovary color: Close to 144A.

*Seed/fruit.*—Seed and fruit development has not been observed.

Disease/pest resistance: Plants of the new Zonal *Geranium* have not been observed to be resistant to pathogens and pests common to Zonal *Geraniums.*

Garden performance: Plants of the new Zonal *Geranium* have been observed to tolerate rain, wind, and temperatures ranging from 5 to 30° C. and have demonstrated good garden performance. Plants of the new Zonal *Geranium* have been observed to flower well under partial shade conditions.

It is claimed:

1. A new and distinct cultivar of Zonal *Geranium* plant named 'Shalet', as herein illustrated and described.

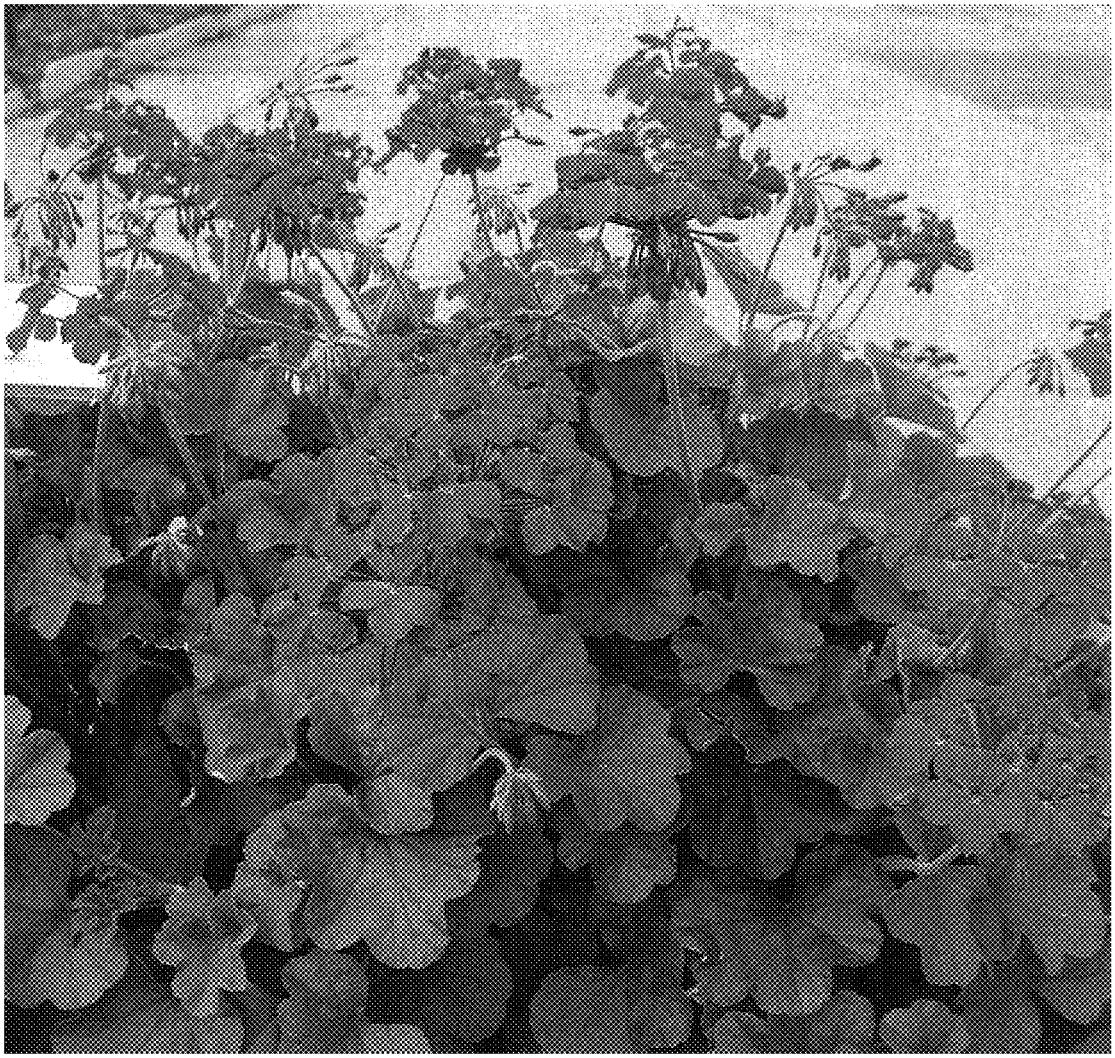

* * * * *